United States Patent [19]

Kurooka et al.

[11]  4,166,767

[45]  Sep. 4, 1979

[54] INSOLUBILIZED ANTIBODY

[75] Inventors: Shigeru Kurooka, Fujiidera; Noriyuki Sunahara, Kyoto, both of Japan

[73] Assignee: Dainippon Pharmaceutical Co., Ltd., Osaka, Japan

[21] Appl. No.: 778,244

[22] Filed: Mar. 16, 1977

[30]  Foreign Application Priority Data

Mar. 25, 1976 [JP]  Japan .................................. 51-33333
Nov. 25, 1976 [JP]  Japan ................................ 51-141879

[51] Int. Cl.² .................... G01N 31/00; A61K 39/00; G01N 31/14
[52] U.S. Cl. ........................................ 435/7; 435/824; 435/837; 435/839; 435/849; 435/857; 435/862; 435/883; 435/885; 435/911; 435/938; 435/942
[58] Field of Search .................. 195/99, 101, 103.5 A, 195/57, 59, 63; 424/12; 23/230 B

[56]  References Cited

U.S. PATENT DOCUMENTS

| 3,654,090 | 4/1972 | Schuurs et al. | 424/12 |
|---|---|---|---|
| 3,850,752 | 11/1974 | Schuurs et al. | 195/63 X |
| 3,912,805 | 10/1975 | Cayzer et al. | 194/103.5 A |
| 3,962,413 | 6/1976 | George et al. | 424/12 |

FOREIGN PATENT DOCUMENTS 49-110885  10/1974  Japan .

*Primary Examiner*—David M. Naff
*Attorney, Agent, or Firm*—Stevens, Davis, Miller & Mosher

[57]  ABSTRACT

An insolubilized antibody suitable for an enzyme immuno assay or radio immuno assay, which has characteristic infrared absorptions at around 1,040 cm$^{-1}$, 1,540 cm$^{-1}$ and 1,640 cm$^{-1}$ and is prepared by chemically binding an antibody to cell wall debris of bacteria or yeasts whose shape is globular or rod-like. There is further disclosed an enzyme immuno assay or radio immuno assay using the insolubilized antibody and a kit containing the insolubilized antibody.

24 Claims, 16 Drawing Figures

INSOLUBILIZED ANTIBODY

The present invention relates to an insolubilized antibody useful for an Exzyme Immuno Assay (hereinafter, referred to as "EIA") or Radio Immuno Assay (hereinafter, referred to as "RIA"). More particularly, it relates to the novel insolubilized antibody bound to cell walls of bacteria or yeasts whose shape is globular or rod-like, and an assay method using the insolubilized antibody and further a kit containing the insolubilized antibody.

The EIA or RIA is generally carried out by subjecting an antigen labeled with an enzyme or radio isotope, an unlabeled antigen (i.e. the substance to be measured) and an antibody to the competitive antigen-antibody reaction in a buffered solution, separating the labeled antigen bound to the antibody and the free labeled antigen (i.e. the labeled antigen to which no antibody is bound), and then determining the amount of the unlabeled antigen (i.e. the substance to be measured). The determination of the unlabeled antigen can be carried out by measuring the enzyme activity or radio activity of the labeled antigen bound to the antibody or of the free labeled antigen and calculating therefrom. The assay method has been described in detail in various literatures, for instance, in U.S. Pat. Nos. 3,654,090, 3,839,153 and 3,850,752 and Clinical Chemistry, Vol. 19 (2), pages 146–186 (1973).

The EIA or RIA should be done in a high sensitivity, accuracy and efficiency to obtain the quantitative data. The efficiency of the EIA or RIA depends largely on the separation method of the labeled antigen bound to the antibody (B) and the free labeled antigen (F) after the antigen-antibody reaction (hereinafter, referred to as "F/B separation method").

There have hitherto been known the following F/B separation methods.

(1) The separation is effected by promoting the secondary agglomeration of the antigen-antibody complex produced by the antigen-antibody reaction.

(2) It is effected by reacting the second antibody to the reaction product of the antigen-antibody reaction (i.e. a double antibody method).

(3) It is effected by using an insolubilized antibody prepared by binding an insoluble substance to an antibody (i.e. an insolubilized antibody method).

The method (1) is applicable when the antigen is a high molecular compound. Accordingly, this method is applicable merely to a specific case, and moreover, it has a defect that too much time is required for the secondary agglomeration.

The double antibody method (2) also requirs a long period of time because the antigen-antibody reaction is carried out twice, and moreover, it has a defect that an undesirable side reaction occasionally occurs when the second antibody is added.

The insolubilized antibody method is the best method, and the present invention is concerned with this method and provides an improved insolubilized antibody.

The insolubilized antibody usable for the EIA or RIA should preferably satisfy the following conditions.

(a) The insolubilized antibody does not inhibit the antigen-antibody reaction.

(b) The insolubilized antibody has a suitable specific gravity so that it can give a uniform and stable suspension and has an exposed area of the reactive group of the antibody as large as possible.

(c) The antigen-antibody complex prepared by the reaction of the insolubilized antibody and the antigen can easily be separated by centrifugation at a low rotary speed or by filtration.

(d) The insolubilized antibody does not adhere to the wall of the devices such as pipette.

There have hitherto been known some insolubilized antibodies which are obtained by binding the antibody to dextran derivatives or cellulose derivatives (U.S. Pat. Nos. 3,839,153 and 3,645,852), but these known insolubilized antibodies do not necessarily satisfy the conditions above-mentioned.

As the results of the present inventors' extensive studies, it has been found that the desired insolubilized antibody satisfying all of the above conditions (a) to (d) can be obtained by chemically binding cell walls of bacteria or yeasts to the antibody.

It has been disclosed in Japanese Laid Open Publication (without examination) No. 110885/1974 that an insolubilized enzyme obtained by binding an enzyme to some moldfungi is useful for the preparation of glucose, but the object of the present invention is essentially different from that of the above invention. Besides, it has experimentally been confirmed by the present inventors that when the antibody is bound to some moldfungi such as *Penicillium chrysogenum* or *Aspergillus niger* or cell walls thereof, the bound antibody can not give a uniform suspension and can not be applied to the EIA or RIA.

An object of the present invention is to provide an improved insolubilized antibody useful for the EIA or RIA.

Another object of the invention is to provide an improved EIA or RIA method using the improved insolubilized antibody.

A further object of the invention is to provide a kit containing the improved insolubilized antibody useful for the EIA or RIA.

These and other objects of the invention will be apparent from the following description.

The insolubilized antibody of the present invention can be prepared by chemically binding the antibody to cell walls of bacteria or yeasts whose shape is globular or rod-like.

Any kinds of bacteria or yeasts whose shape is globular or rod-like can be used in the present invention, regardless the kinds of the products or the pathogenicity of the microorganisms. For instance, the cell walls of *Lactobacillus plantarum* ATCC 8014 is usable like these of other strains belonging to the same species. Likewise, alternatively, there may be used the cell walls of *Micrococcus roseus* ATCC 9815 and of *Micrococcus lysodeiticus* ATCC 4698 which belongs to the same genus but to the species different from that of *Micrococcus roseus*, and further, the cell walls of *Saccharomyces cerevisiae* (a commercially available baker's yeast) as used in Example 7 as disclosed hereinafter and of *Lactobacillus plantarum* ATCC 8014 which belongs to the different class to that of *Saccharomyces cerevisiae*.

The bacteria usable in the present invention are microorganisms of the order Eubacteriales, for instance, the microorganisms of the genus Streptococcus, Staphylococcus, Micrococcus, Lactobacillus, Bacillus, Escherichia and Achromabacter. Suitable examples of the bacteria are Streptococcus faecalis, Streptococcus salivarius, Streptococcus mutans, Staphylococcus aureus, Micrococcus lysodeiticus, Micrococcus roseus, Lactobacillus plantarum, Bacillus subtilis, Bacillus megatherium, Escherichia coli and Achromabacter acquamarinus.

The yeasts usable in the present invention are, for instance, microorganisms of the genus Saccharmomyces such as Saccharomyces cerevisiae, the genus Pichia such as Pichia polymorpha, the genus Schizosaccharomyces such as Schizosaccharomyces pombe, or the like. The most suitable one is Saccharomyces cerevisiae which is easily available.

The cell walls of the bacteria or yeasts can be prepared by treating the cells of the microorganisms by various methods, such as a physical treatment (e.g. the treatment with a homogenizer or ultrasonicator), an enzymatic treatment (e.g. digestion with trypsin), a chemical treatment (e.g. boiling in a diluted alkaline solution), or a combination of these treatments.

The antibody used in the present invention may be prepared by immunizing an appropriate animal, such as rabbit, horse, goat, guinea pig or cattle, with the corresponding antigen-containing adjuvant to produce the antibody in the sera. Besides, the antibody against haptens may be prepared by absorbing or binding the haptens to a high molecular substance (e.g. albumin) and then immunizing the animal with the resultant substance-containing adjuvant.

The antigen used for the preparation of the antibody is, for instance, hormones such as angiotensin I, insulin, tri- or tetra-iodothyronine (hereinafter, referred to as "T₃" or "T₄") or human chorionic gonadotropin (hereinafter, referred to as "HCG"); bacteria; enzymes; virus; virus-specific antigens (e.g. virus hepatitis B); tumor antigens (e.g. α-fetprotein or carcino embryonic antigen); immunoglobulins (e.g. IgG or IgE); human- or bovine-serum albumin (hereinafter, referred to as "HSA" or "BSA"); or haptens such as diphenylhydantoin (hereinafter, referred to as "DPH"), haloperidol [i.e. 1-(3-p-fluorobenzoylpropyl)-4-p-chlorophenyl-4-hydroxypiperidine], testosterone, phenobarbital or the like. Besides, the haptens include some compounds having a chemical structure partially common to that of the substance to be measured (i.e. the unlabeled antigen). For instance, in case of measuring the quantity of haloperidol, a compound having 3-(p-fluorobenzoyl)propionyl group other than haloperidol may be used as the haptens, and the antibody to this compound is reacted with haloperidol to form an antigen-antibody complex.

The chemical binding of the antibody to the cell wall of bacteria or yeasts may be performed by reacting them in the presence of a binding agent. The binding agent includes various conventional binding agents as disclosed in Methods of Enzymology, Vol. 11, pages 617–641, Academic Press, New York, 1967. Suitable examples of the binding agent are glutaraldehyde, epichlorohydrin, toluene-2,4-diisocyanate, carbodiimide, or the like. Among them, glutaraldehyde is the most suitable on to be used.

Alternatively, the binding of the cell wall of bacteria or yeasts to the antibody can be performed without using any binding agent, when the cell wall is oxidized with an oxidizing agent such as sodium periodate to give an oxidized cell wall. The antibody is reacted with the oxidized cell wall and then the resultant is reduced. In this oxidation method, the amino groups contained in the cell wall may optionally be protected first with an appropriate agent, such as 2,4-dinitrofluorobenzene, prior to the oxidization, in order to prevent the undesirable polymerization of the cell walls.

According to this oxidization method developed by the present inventors, the binding of the cell wall to the antibody will probably proceed in the following manner.

The sugar components of the cell wall are oxidized to form an aldehyde group, and the aldehyde group thus formed is reacted with the amino groups contained in the antibody to form a Schiff's base, and the binding is more strengthened by reducing the above resultant. In this method, the unreacted antibody remaining in the reaction mixture can be favorably recovered by adding a new oxidized cell wall to the mixture.

The insolubilized antibody shows characteristic infrared absorption spectrum, i.e. the absorptions at around 1540 cm$^{-1}$ and 1640 cm$^{-1}$ (A) owing to the group: —NHCO— and the absorption at around 1040 cm$^{-1}$ (B) owing to the group:

contained in the sugar, as shown in the accompanying FIGS. 1 to 4.

The ratio: A/B of the infrared absorptions (transmission) of the insolubilized antibody is always larger than that of the cell wall before bound to the antibody (e.g. the cell wall oxidized or treated with glutaraldehyde). The ratio: A/B is calculated on the basis of the base line combining the absorption at around 1,900 cm$^{-1}$ and the absorption at around 850–900 cm$^{-1}$.

The EIA or RIA using the insolubilized antibody of the present invention may be carried out by subjecting to the competitive immuno reaction between an antigen labeled with an enzyme (e.g. β-D-galactosidase, pancreatic lipase, peroxidase, or glucose oxidase) or a radio isotope (e.g. $^{125}$I, $^{3}$H, or $^{14}$C), an unlabeled antigen (the substance to be measured) and the insolubilized antibody in a buffer solution, separating the resulting antigen-antibody complex by centrifugation, and then measuring the enzyme activity or radio activity of the labeled antigen in the precipitate or the supernatant fluid by a conventional method, by which the EIA or RIA can easily be performed at a high sensitivity within a short period of time.

Thus, in the EIA or RIA using the present insolubilized antibody, the essential reagents are (a) the insolubilized antibody of the present invention, and (b) an labeled antigen for the above antibody.

In addition to the above reagents, a standard substance for preparing a standard calibration curve, and further, in case of EIA, a chromogenic substrate for the enzyme and/or an enzyme reaction-stopping reagent are also optionally employed.

These reagents may preferably be packed in the form of a kit.

The present invention will be illustrated by the following Reference Examples and Examples, but is not limited thereto.

In these examples, the following bacteria and yeasts are used for the preparation of cell walls. These microorganisms are mentioned in the examples merely in the abbreviated name as shown in square brackets: Streptococcus faecalis IFO 14580 [St. faecalis], Staphylococcus aureus Terajima [Sta. aureus], Micrococcus roseus ATCC 9815 [*M. roseus*], *Micrococcus lysodeiticus* ATCC 4698 [*M. lysodeiticus*], *Lactobacillus plantarum* ATCC 8014 [*L. plantarum*], *Bacillus subtilis* IFO 3335 [*B. subtilis*], *Escherichia coli* K-12 [*E. coli*], *Achromobacter aquamarinus* ATCC 14400 [*A. aquamarinus*], *Saccharomyces cerevisiae* (sold by Oriental Yeast Co., Japan) [*S. cerevisiae*], *Pichia polymorpha* IFO 0195 [*P. polymorpha*], and *Schizosaccharomyces pombe* IFO 0346 [*S. pombe*].

Moreover, the following materials used in the examples are products purchased from the commercial sources shown in round brackets:

*E. coli* β-D-galactosidase and hog hepatic esterase (Boehringer Mannheim G.m.b.H., in W. Germany); hog pancreatic lipase, bovine insulin, HCG, T$_3$ and T$_4$ (Sigma Chemical Co., in U.S.A.); HSA (recrystallized 4 times) (Nutritional Biochemicals Co., in U.S.A.); human IgG (AB KABI, in Sweden); $^{125}$I-T$_3$ and $^{125}$I-insulin (Dainabot Radioisotope Lab., Ltd., in Japan); $^3$-H-DPH (New England Nuclear Corp., U.S.A.); anti-HCG rabbit antibody, anti-HSA rabbit antibody and anti-bovine insulin guinea pig antibody (Miles Laboratories Inc., in U.S.A.); $^3$H-testosterone (The Radio Chemical Center Amersham, in England); and $^3$H-haloperidol (C.I.S.: a community of Commissariat a l'Energie Atomique in France, Institute National des Radioelements in Belgium and Centro Ricerche Nucleari in Italy).

Other materials are prepared by the present inventors.

REFERENCE EXAMPLE 1

Preparation of Bacterial Cell Walls

Cells of *L. plantarum* separated from the culture broth were washed well with water and 0.9% NaCl by using a centrifugation and freeze-dried. The freeze-dried cells (15 g) and glass beads (0.17–0.18 mm in diameter, 30 g were suspended in 0.9% NaCl solution (30 ml) and broken (4×30 second, 60 cycle/second) by a homogenizer (B. Braun SS-30 Type) under cooling with dry ice.

After removing the glass beads by a centrifugation (300×g, 30 minutes), the cell debris was centrifuged again (10,000×g, 30 minutes) and washed well with water and freezed-dried.

The freezed-dried cell debris were suspended in a 0.05 M phosphate buffer (1 g/50 ml), digested at 40° C. for 2 hours in the presence of 0.001% tripsin, and centrifuged (9,000×g, 30 minutes). The precipitate thus obtained was digested again with trypsin, washed well with water, and freeze-dried.

About 750 mg of cell walls of *L. plantarum* were obtained (yield 10% from dried cells).

In the same way, prepared were freeze-dried cell walls of *A. aquamarinus*, *Sta. aureus*, *St. faecalis*, *M. roseus*, *B. subtilis* and *E. coli*.

REFERENCE EXAMPLE 2

Preparation of Yeast Cell Walls

Pressed *S. cerevisiae* (250 g) was suspended in water (500 ml), disrupted with glass beads (0.25–0.5 mm in diameter) in DINOMIL (a trade name of a mil sold by Maschin Fabrik) at the speed of 3,000 r.p.m. The disrupted cells were washed well with 1 M NaCl and water alternately, and freeze-dried. About 13 grams of cell walls of *S. cerevisiae* were obtained.

In the same way, cell walls of *P. polymorpha* and *S. pombe* were prepared.

REFERENCE EXAMPLE 3

Preparation of Enzyme Labeled Antigen (A) Glutaraldehyde method

1% Glutaraldehyde (0.25 ml) was added with a constant stirring to 0.05 M phosphate buffer (0.25 ml) containing 3,3-diphenylpropylamine (100 μg) and purified hog pancreatic lipase (1 mg), and stirred for 2 hours. The reaction mixture was passed through a Sephadex G 200 column (1×54 cm) (sold by Pharmacia Fine Chemicals in Sweden), eluted with 0.05 M Tris-HCl—0.1 M KCl buffer solution (pH 8.0) and fractionated (one fraction volume 1.5 ml) to give [3,3-diphenylpropylamine]-[hog pancreatic lipase] complex (enzyme labeled antigen) (7 ml) which was eluted near in the void fractions. The enzyme labeled antigen was kept at 5° C. in the presence of 0.1% BSA.

In the same way, enzyme labeled antigen, [hog hepatic esterase]-[HSA] or -[human serum IgG] complex were prepared from a purified hog hepatic esterase (2 mg) and HSA (2.5 mg), or the esterase (5 mg) and the human serum IgG (3 mg), respectively.

(B) Maleimide method

B-1 [β-D-galactosidase]-[T$_3$] or -[T$_4$] conjugate

A 0.1 N NaOH aqueous solution (50 μl) containing T$_3$ or T$_4$ (made by Sigma Chemical Co., in U.S.A., 0.5 μmole) was mixed with 0.05 M phosphate buffer (pH 7.0, 1 ml) and thereto was added dropwise with stirring a solution of 6-maleimide-n-capronic acid N-succinimide ester (0.5 μmole) in tetrahydrofuran (25 μl). The mixture was reacted at room temperature for 10 minutes, and thereto was added a 0.2 M citrate-phosphate buffer (pH 4.3, 40 μl). The resulting precipitates were separated by centrifugation (2000×g, 10 minutes) and was washed with a 0.05 M citrate-phosphate buffer (pH 4.3, 1 ml) by centrifugation. To the precipitates thus obtained was added a 0.05 M phosphate buffer (pH 7.0, 1 ml) and thereto was further added with stirring β-D-galactosidase (0.19 nmol, i.e. 100 μg). After stirring the mixture for 10 minutes, a 0.1 M glycine-NaOH buffer (pH 10.3, 5 ml) was added thereto. The mixture was filtered through a Diaflo-membrane PM 30 (made by Amicon Corp in U.S.A.) to remove the unreacted 6-maleimide-n-capronic acid N-succinimide ester or unreacted T$_3$ or T$_4$. The resulting residue was further washed twice with a 0.05 M phosphate buffer (pH 7.0, 3 ml) and then was dissolved in a 1% BSA—0.05 M phosphate buffer (pH 7.0, 1.5 ml).

B-2 [3,3-Diphenylpropylamine]-[β-D-galactosidase]

A solution of N-(3,3-diphenylpropyl)aminocarbonyl-methylmaleimide (500 μg) in tetrahydrofuran (25 μl) was added dropwise with stirring to a 0.05 M phosphate buffer (pH 8.0, 2 ml) containing β-D-galactosidase (1 mg), stirred for 1 hour at room temperature, filtered through a Diaflow membrane PM 30 and washed 3 times with a 0.02 M phosphate buffer (pH 7.0, 4 ml). The residue was dissolved in a 0.2% BSA—0.05 M phosphate buffer (pH 7.0).

B-3 [HCG]-[β-D-galactosidase]

HCG (600 units) acylated with m-maleimidobenzoyl N-hydroxysuccinimide ester was added to a 0.05 M phosphate buffer (pH 8.0, 1 ml) containing β-D-galactosidase (100 μg), stirred for 1 hour at room temperature, filtered through a Diaflow membrane, washed as described in B-2, and the residue was dissolved in a 1% BSA-0.05 M phosphate buffer (pH 7.0, 1 ml).

B-4 [Bovine insulin]-[β-D-galactosidase]

It was prepared by the method described in J. Biochem., Vol. 79, page 235 (1976).

(C) Diazocoupling method

[β-D-Galactosidase]-[m-diazophenobarbital]

A solution of m-aminophenylbarbital (1.5 mg), potassium bromide (170 μg) and 36% HCl (2 μl) in water (0.23 ml) was mixed with a solution of sodium nitrite (570 μg) in water (80 μl) under ice cooling and kept for 1 hour. The reaction mixture (80 μl) mixed with a 0.01 M sodium borate solution (4 ml) was added to a 0.02 M potassium phosphate buffer (pH 7.0, 2 ml) containing β-D-galactosidase (500 μg) and stirred for 1 hour under ice cooling. The reaction mixture was filtered through a Diaflow membrane PM 30 (Amicon Corp. in U.S.A.), and the resulting residue was washed 3 times with a 0.9% NaCl—0.02 M Tris-HCl (pH 7.0, each 10 ml). The residue was dissolved in a 0.2% BSA—0.9% NaCl—0.1% NaN₃—0.02 M Tris-HCl (pH 7, 20 ml) (400 assays).

EXAMPLE 1

Preparation of Insolubilized Antibody

Figure 1:
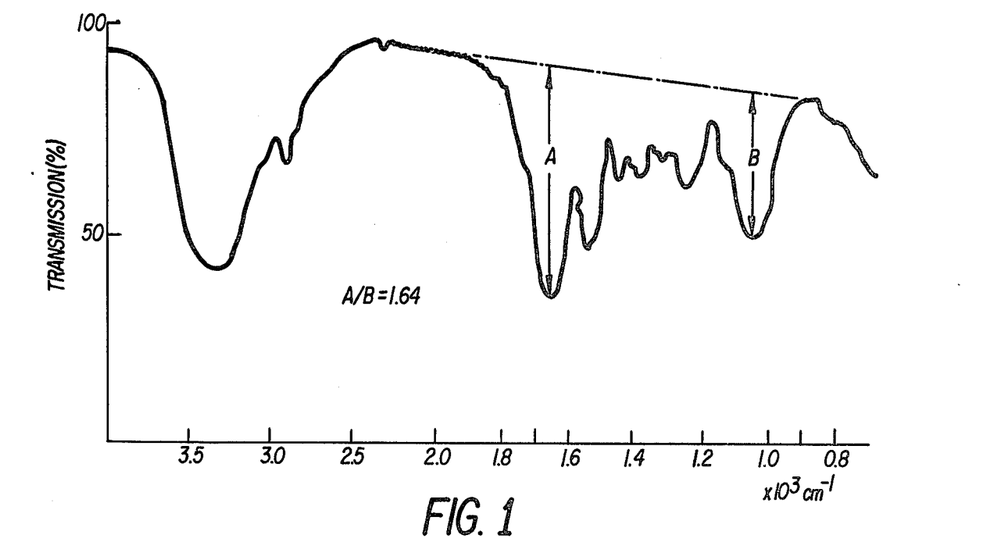

L. plantarum cell walls (125 mg) prepared as described in Reference Example 1 were suspended in water (2.5 ml), mixed with anti-diphenylacetyl-BSA rabbit antibody solution (2.5 ml) [IgG fraction; protein 10 mg/0.05 M phosphate buffer (pH 7.0) 1 ml], water (2.5 ml) and a 0.1 M phosphate buffer (pH 7.0, 2.5 ml), and to this solution was added dropwise with stirring a 2.5% glutaraldehyde aqueous solution (2.5 ml). After stirring for 1 hour, the mixture was centrifuged (2,000×g, 10 minutes), and the precipitate was washed three times with a 0.9% NaCl—0.02 M Tris-HCl buffer (pH 7.0, each 5 ml) to give [L. plantarum cell walls]-[anti-diphenylacetyl-BSA rabbit antibody]. A part of the insolubilized antibody thus obtained was freeze-dried and subjected to analysis of infrared spectrum. The results are shown in FIG. 1. The insolubilized antibody was suspended in a 0.1% BSA—0.9% NaCl—0.02 M Tris-HCl buffer (pH 7.0) to give a 1% cell walls—0.1% BSA solution, which was sonicated (20 kc/s, 30 seconds) and then used for EIA or RIA.

In the same manner as described above except that no antibody was added, L. plantarum cell walls treated with glutaraldehyde were prepared. The infrared spectrum of the cell walls is shown in FIG. 2.

Figure 2:
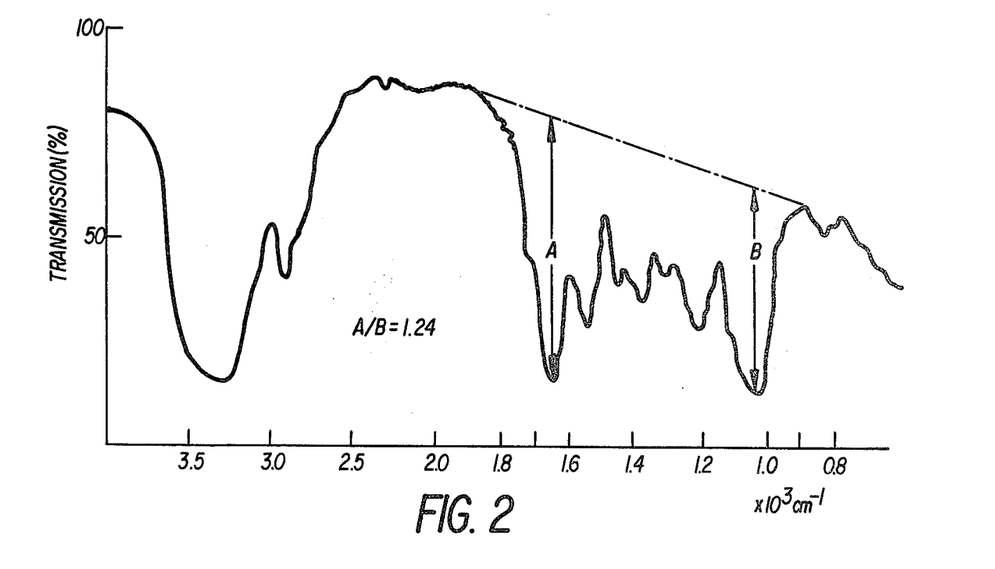

As is made clear from FIGS. 1 and 2, A/B ratio of L. plantarum cell walls treated with glutaraldehyde was 1.24 and that of [L. plantarum cell walls]-[anti-diphenylacetyl-BSA rabbit antibody] was 1.64, which indicates the formation of cell walls—antibody complex.

When untreated L. plantarum cell walls were mixed with the antibody and followed by washing, neither increase in A/B ratio nor potency of antibody was observed.

In the similar way, the following insolubilized antibodies were prepared.

[L. plantarum cell walls]-[anti-HCG rabbit antibody]

[L. plantarum cell walls]-[anti-human IgG rabbit antibody]

[L. plantarum cell walls]-[anti-HSA rabbit antibody (without BSA)]

[L. plantarum cell walls]-[anti-T₃-BSA rabbit antibody]

[L. plantarum cell walls]-[anti-bovine thyroglobulin guinea pig antibody]

[S. cerevisiae cell walls]-[anti-bovine insulin guinea pig antibody]

[B. subtilis cell walls]-[anti-HCG rabbit antibody]

[E. coli cell walls]-[anti-human IgG rabbit antibody]

[M. roseus cell walls]-[anti-HSA rabbit antibody (without BSA)]

[St. faecalis cell walls]-[anti-T₃-BSA rabbit antibody]

[A. aquamarinus cell walls]-[anti-diphenylacetyl-BSA rabbit antibody]

EXAMPLE 2

Preparation of insolubilized antibody

Figure 3:
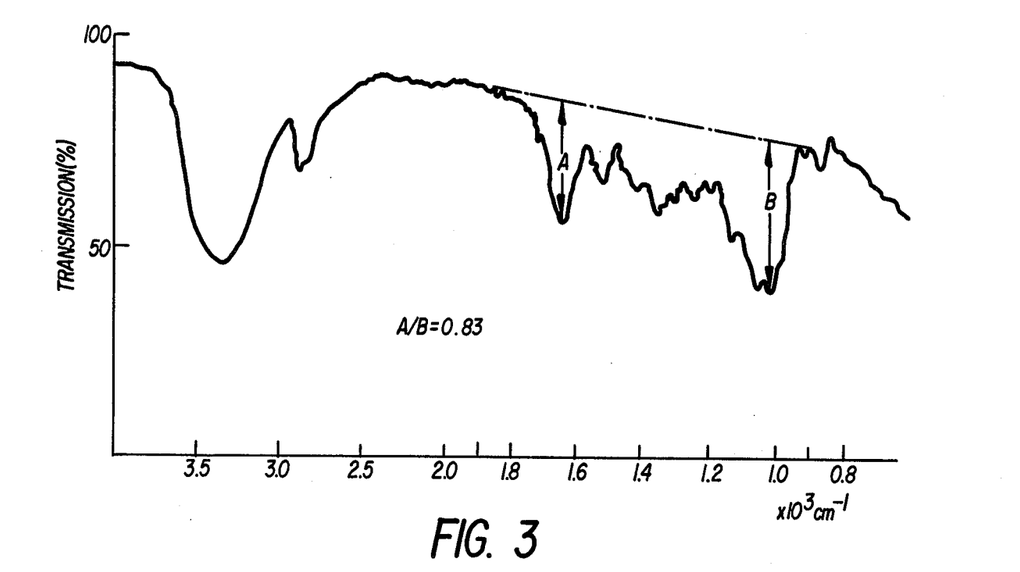

S. cerevisiae cell walls (20 mg) prepared in Reference Example 2 were added to a mixture of 0.3 M NaHCO₃ (2 ml) and a 1% solution of 2,4-dinitrofluorobenzene in ethanol (0.2 ml), and kept for 1 hour at room temperature. After addition of 0.1 M NaIO₄ (2 ml), the mixture was allowed to stand in dark at room temperature for 48 hours, followed by washing well with water to give oxidized cell walls. (The infrared spectrum of the oxidized S. cerevisiae cell walls thus obtained is shown in FIG. 3)

The oxidized cell walls were mixed with a 1 M Na₂CO₃ buffer (pH 9.0, 0.1 ml) and anti-diphenylacetyl-BSA rabbit antibody (0.2 ml) [IgG fraction; protein 10 mg/0.05 M phosphate buffer (pH 7.0) 1 ml] and further added water so as to make the total volume 1 ml. The mixture was stirred at 4° C. for 24 hours and centrifuged (2,000×g, 10 minutes). The precipitate was washed well with a 0.02 M Tris-HCl buffer (pH 7.0) and a 0.9% NaCl aqueous solution, alternatively. The precipitate was suspended in a 1% NaBH₄ aqueous solution (1 ml), and the suspension was allowed to stand for 15 minutes, and washed with water to give [S. cerevisiae cell walls]-[anti-diphenylacetyl-BSA rabbit antibody].

Figure 4:
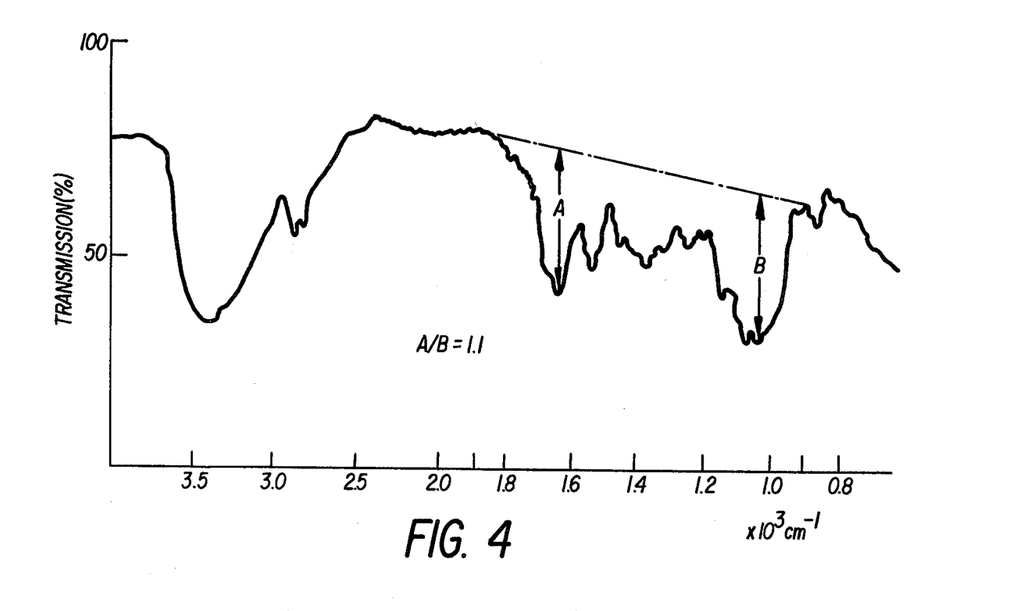

The insolubilized antibody thus obtained showed the infrared spectrum as shown in FIG. 4. The insolubilized antibody was suspended in a 0.9% NaCl—0.1% BSA—0.02 M Tris-HCl buffer (pH 7.0) to give a 1% cell walls—0.1% albumin solution, which was used for EIA or RIA.

In the same manner as described above, the following insolubilized antibodies were prepared.

[S. cerevisiae cell walls]-[anti-bovine insulin guinea pig antibody]

[S. cerevisiae cell walls]-[anti-teststerone-3-oxime-BSA rabbit antibody]

[S. cerevisiae cell walls]-[anti-3-(p-fluorobenzoyl)propionyl-BSA guinea pig antibody]

[L. plantarum cell walls]-[anti-diphenylacetyl-BSA rabbit antibody]

[B. subtilis cell walls]-[anti-diphenylacetyl-BSA rabbit antibody]

[Sta. aureus cell walls]-[anti-diphenylacetyl-BSA rabbit antibody]

[E. coli cell walls]-[anti-diphenylacetyl-BSA rabbit antibody]

EXAMPLE 3

Preparation of anti-phenobarbital insolubilized antibody

Anti-phenobarbital rabbit serum was prepared as described by H. Satoh et al (J. Biochem., Vol 73, page 1115 (1973) except that BSA-m-diazophenobarbital was used as a hapten. Anti-phenobarbital rabbit antibody was prepared from the antiserum by ammonium sulfate fractionation (0–48%) and dialysis against a 0.05 M phosphate buffer.

Anti-phenobarbital rabbit antibody (23 mg) and *S. cerevisiae* cell walls (25 mg) (prepared as described in Reference Example 2) were suspended in a 0.05 M sodium acetate buffer (pH 4.9, 3 ml) and 25% glutaraldehyde (70 μl) was thereto added dropwise with stirring, and the mixture was kept at room temperature for 2 hours. The reaction mixture was centrifuged (3,500×g, 20 minutes) and the precipitate was washed well 2 times with a 0.9% NaCl—0.02 M Tris-HCl buffer (pH 7.0, each 10 ml) by centrifugation. The obtained [*S. cerevisiae* cell walls]-[anti-phenobarbital rabbit antibody] was suspended in a 0.2% BSA—0.9% NaCl—0.1% NaN$_3$—0.02 M Tris-HCl buffer (pH 7.0, 5.2 ml), sonicated (19 kc/s, 30 seconds), and used for EIA of serum phenobarbital.

EXAMPLE 4

General method of EIA or RIA using insolubilized antibodies (A) Reagents:
(a) 0.9% NaCl—0.02 M Tris-HCl buffer solution (pH 7.0)
(b) Standard antigen
(The standard antigen was prepared by diluting the antigen with the above buffer (a) by a two fold dilution method)
(c) Enzyme or isotope labeled antigen: a fixed amount
(The fixed amount of enzyme labeled antigen is shown by the variation of the optical density (hereinafter, referred to as "OD") during a fix period of time when measured by the method as shown in the following item (c), wherein the enzyme activity of the labeled antigen which can bind to the insolubilized antibody is measured).
(d) Insolubilized antibody; a fixed amount
(The fixed amount of antibody means the amount of the antibody bound to cell walls of which 50-70% can bind to the fixed amount of the labeled antigen. About 500 μg of cell walls are preferably used for 1 assay)

(B) Assay procedure
Into glass centifuge tubes (1.3×10 cm) X$_1$ ... X$_n$ for standard antigen calibration curve and Y$_1$ ... Y$_m$ for samples, was added the buffer solution (a) (1 ml). Prescribed amounts (prepared by a two fold dilution method) of the standard antigen (b) were added to the tubes X$_1$-X$_n$ and samples (50 μl) were added to other tubes Y$_1$-Y$_m$, and then the fixed amount of the labeled antigen (c) and the insolubilized antibody (d) (each 50 μl) were added to all the tubes and the tubes were kept at 5° C. for a fixed time, followed by centrifugation (2,000×g, 10 minutes). The enzyme or radio activity of the labeled antigen in the supernatant or the precipitate was measured. From the data, a standard calibration curve was drawn, from which the levels of antigen in the samples (Y$_1$-Y$_m$) were calculated.

(C) Determination of enzyme or radio activity
The activity of hog pancreatic lipase or hog hepatic esterase was measured by a colorimetric method using 3-butyroyloxy-1,2-bis(butyroylthio)propane as a substrate (cf. U.S. Pat. No. 3,986,930). The activity of β-D-galactosidase was measured by a fluorometric method using 4-methylumbelliferyl-β-D-galactopyranoside as a substrate [cf. J. Biochem., Vol. 78, page 235 (1975)] or a colorimetric method using O-nitrophenyl-β-D-galactopyranoside as a substrate [cf. Biochem. Biophys. Acta, Vol. 403, page 131 (1975)].

Radio activity of $^{125}$I was measured by an automatic well type scintillation counter AL 201 (sold by DAINABOT—SHIMAZU CO., in Japan). Radio activity of $^3$H was measured by TRI-CARB Liquid Scintillation Spectrophotometer, Type 3380 (sold by Packard Instrument Co.).

EXAMPLE 5

Measurement of DPH

Figure 5:
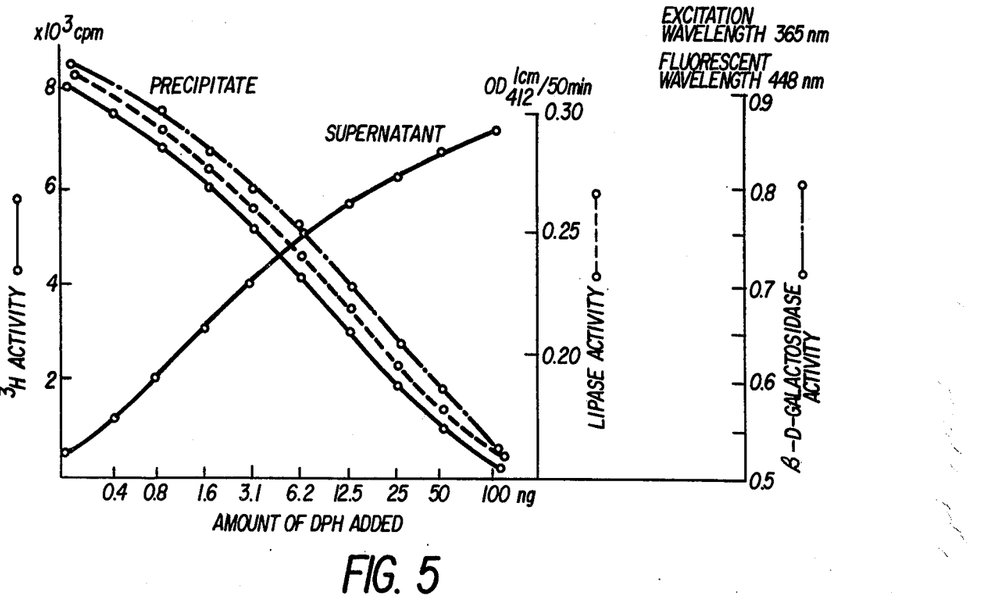

According to the general method as described in Example 4, the EIA and RIA were carried out under the following conditions. From the resulting data, there was drawn the calibration curve as shown in FIG. 5.

Insolubilized antibody

[*S. cerevisiae* cell walls]-[anti-diphenylacetyl-BSA rabbit antibody] which was prepared in Example 2.

Labeled antigen

[3,3-Diphenylpropylamine]-[hog pancreatic lipase] which was prepared in Reference Example 3, (A) ... OD$_{412}^{1\ cm}$/30 minutes=0.6.
[3,3-Diphenylpropylamine]-[β-D-galactosidase] which was prepared in Reference Example 3, (B-2) ... OD$_{448}^{1\ cm}$/20 minutes=1.8
$^3$H—DPH ... 100 pg (10,000 cpm)

UNLABELED ANTIGEN

Standard DPH ... 0–100 ng
The time of the antigen-antibody reaction ... 30 minutes As is made clear from FIG. 5, in both EIA and RIA, the measurement of DPH (0.4–100 ng) could be finished within 1.5 hours. On the other hand, according to the double antibody method, the measurement required about 2 days.

EXAMPLE 6

Measurement of DPH

In the same manner as described in Example 5, there was measured DPH on the sera (each 10 μl) of normal persons and of patients to whom DPH was orally administered.

The DPH in the same samples was measured by a gas chromatography (hereinafter, referred to as "G.C.").

The results are shown in the following Table 1.

Table 1

| Sample | EIA* (μg/ml) | RIA (μg/ml) | G.C. (μg/ml) |
|---|---|---|---|
| Serum of normal persons (10 persons) | 0 | 0 | 0 |
| Serum of patient A | 3.3 | 3.4 | 3.1 |
| B | 2.8 | 2.3 | 2.7 |
| C | 1.2 | 1.3 | 1.0 |
| D | 1.5 | 1.8 | 1.6 |
| E | 1.5 | 1.5 | 1.6 |
| F | 2.6 | 2.8 | 2.5 |
| G | 1.7 | 1.8 | 1.6 |
| H | 1.2 | 1.6 | 1.4 |
| I | 2.4 | 2.6 | 2.4 |
| J | 0.3 | 0.1 | 0 |

*[3,3-Diphenylpropylamine]-[β-D-galactosidase] was used as the labeled antigen.

As is made clear from the above Table 1, the quantitative data of these three methods coincided each other quite well.

EXAMPLE 7

Measurement of DPH

The RIA was carried out in the same manner as described in Example 5 except that the following insolubilized antibodies prepared in Example 2 were used instead of [S. cerevisiae cell walls]-[anti-diphenylacetyl-BSA rabbit antibody]. [L. plantarum cell walls]-[anti-diphenylacetyl-BSA rabbit antibody], [B. subtilis cell walls]-[anti-diphenylacetyl-BSA rabbit antibody], [Sta. aureus cell walls]-[anti-diphenylacetyl-BSA rabbit antibody], or [E. coli cell walls]-[antidiphenylacetyl-BSA rabbit antibody].

As the results, the same calibration curve of DPH as in FIG. 5 could be drawn.

Example 8

Measurement of HCG

Figure 6:
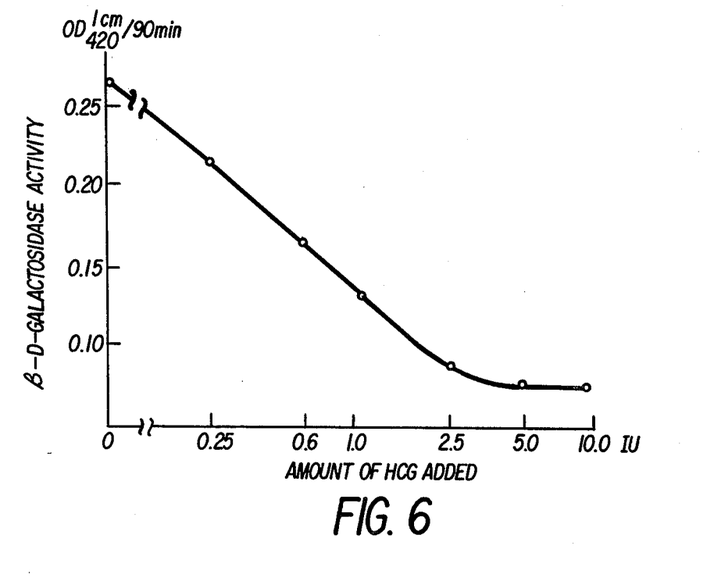

According to the general method as described in Example 4, the EIA was carried out under the following conditions. From the resulting data, there was drawn the calibration curve of HCG as shown in FIG. 6.

Insolubilized antibody

[L. plantarum cell walls]-[anti-HCG rabbit antibody] which was prepared in Example 1.

Labeled antigen

[HCG]-[β-D-galactosidase] which was prepared in Reference Example 3, (B-3) . . . $OD_{420}^{1\ cm}/90$ minutes = 0.6.

Unlabeled antigen

Standard HCG . . . 0–10 IU

The time of the antigen-antibody reaction . . . 30 minutes

As is made clear from FIG. 6, the measurement of HCG (0.25–2.5 IU) could be finished within 1.5 hours. On the other hand, according to the double antibody method, the measurement required about 2 days.

EXAMPLE 9

Measurement of HSA

Figure 7:
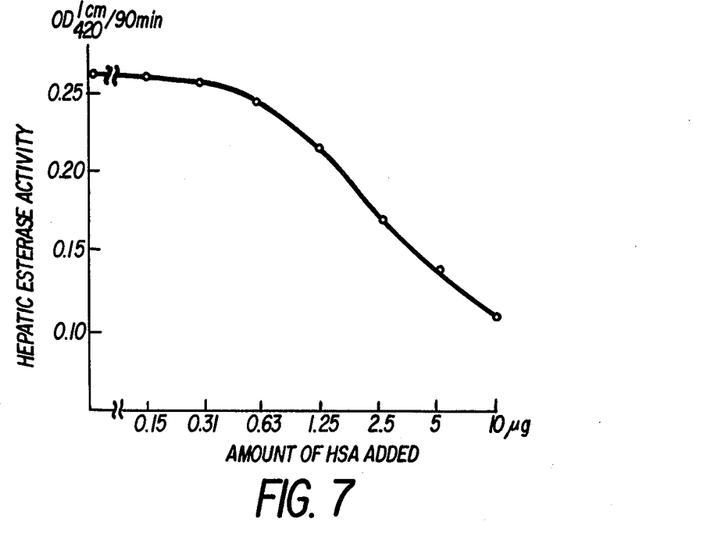

According to the general method as described in Example 4, the EIA was carried out under the following conditions. From the resulting data, there was drawn the calibration curve of HSA as shown in FIG. 7.

Insolubilized antibody

[L. plantarum cell walls]-[anti-HSA rabbit antibody] which was prepared in Example 1.

Labeled antigen

[HSA]-[hog hepatic esterase] which was prepared in Reference Example 3, (A) . . . $OD_{412}^{1\ cm}/15$ minutes = 0.9

Unlabeled antigen

Standard HSA . . . 0–10 μg

The time of the antigen-antibody reaction . . . 30 minutes

As is made clear from FIG. 7, the measurement of HSA (0.6–10 μg) could be finished within 1.5 hours.

EXAMPLE 10

Measurement of $T_3$

Figure 8:
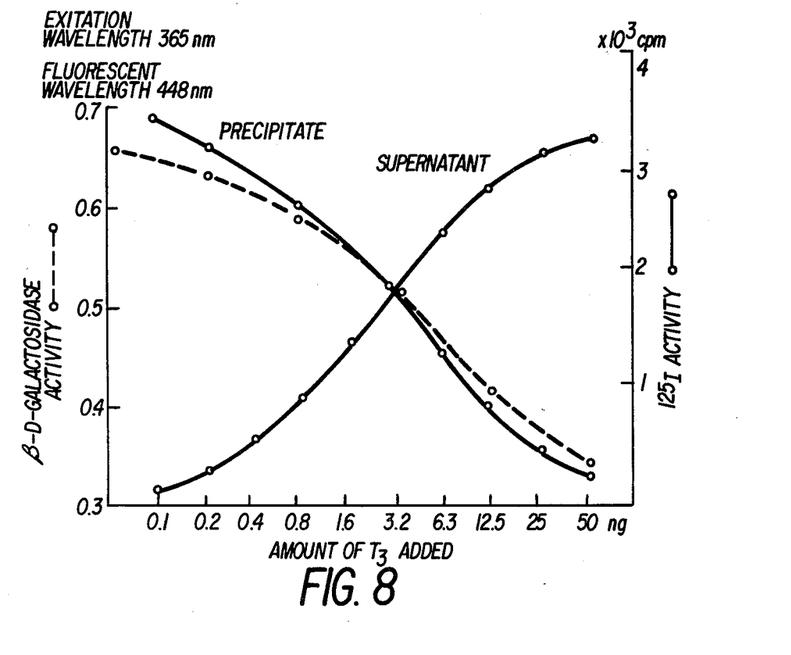

According to the general method as described in Example 4, the EIA were carried out under the following conditions. From the resulting data, there was drawn the calibration curve of $T_3$ as shown in FIG. 8.

Insolubilized antibody

[L. plantarum cell walls]-[anti-$T_3$-BSA rabbit antibody] which was prepared in Example 1.

Labeled antigen

[$T_3$]-[β-D-galactosidase] which was prepared in Reference Example 3, (B-1) . . . $OD_{448}^{1\ cm}/20$ minutes = 1.4

[$^{125}$I]-[$T_3$] . . . 3,500 cpm

Unlabeled antigen

Standard $T_3$ . . . 0–50 ng

The time of the antigen-antibody reaction . . . 30 minutes

As is made clear from FIG. 8, in both of EIA and RIA, the measurement of $T_3$ (0.1–50 ng) could be finished within 1.5 hours. On the other hand, according to the double antibody method, the measurement required about 2 days.

EXAMPLE 11

Measurement of insulin

Figure 9:
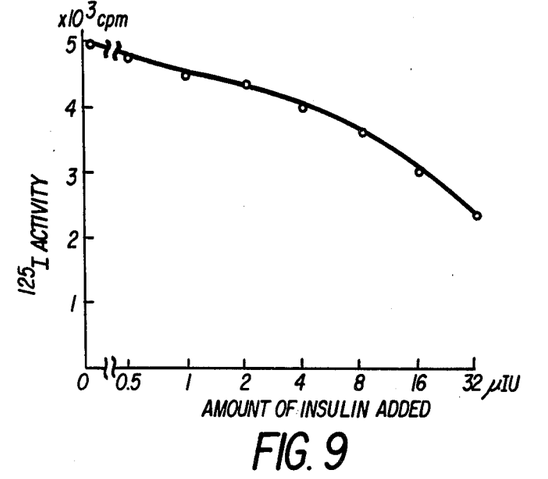

According to the general method as described in Example 4, the RIA was carried out under the following conditions. From the resulting data, there was drawn the calibration curve of a bovine insulin as shown in FIG. 9.

Insolubilized antibody

[S. cerevisiae cell walls]-[anti-bovine insulin guinea pig antibody] which was prepared in Example 1.

Labeled antigen

[$^{125}$I]-[hog insulin] . . . about 10,000 cpm

Unlabeled antigen

Standard hog insulin . . . 0–32 μIU

The time of the antigen-antibody reaction . . . 15 hours

As is made clear from FIG. 9, the measurement of the hog insulin (0.5–32 μIU) could be finished within a day. On the other hand, according to the double antibody method, the antigen-antibody reaction required 48 hours (the first reaction: 24 hours, the second reaction: 24 hours).

EXAMPLE 12

Measurement of insulin

Example 11 was repeated except that [S. cerevisiae cell walls]-[anti-bovine insulin guinea pig antibody] prepared in Example 2 was used instead of [S. cerevisiae cell walls]-[anti-bovine guinea pig antibody] prepared in Example 1. The same result as in Example 11 was obtained.

EXAMPLE 13

Measurement of insulin

Figure 10:
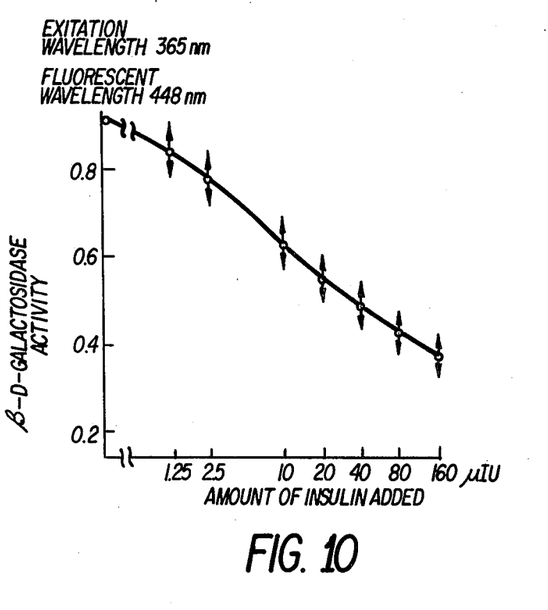

According to the general method as described in Example 4, the EIA was carried out under the following conditions. From the resulting data, there was drawn the calibration curve of insulin as shown in FIG. 10.

Insolubilized antibody

S. cerevisiae cell walls]-[anti-bovine insulin guinea pig antibody] which was prepared in Example 2.

Labeled antigen

[Bovine insulin]-[β-D-galactosidase] which was prepared in Reference Example 3, (B-4) . . . $OD_{420}^{1\ cm}$/30 minutes=0.016

[Note]: The determination of this labeled antigen was carried out by a colorimetry, and the measurement of the enzyme activity in the EIA was carried out by a fluorophotometry.

Unlabeled antigen

Standard bovine insulin . . . 0–160 μIU
The time of the antigen-antibody reaction . . . 15 hours.

EXAMPLE 14

Measurement of testosterone

Figure 11:
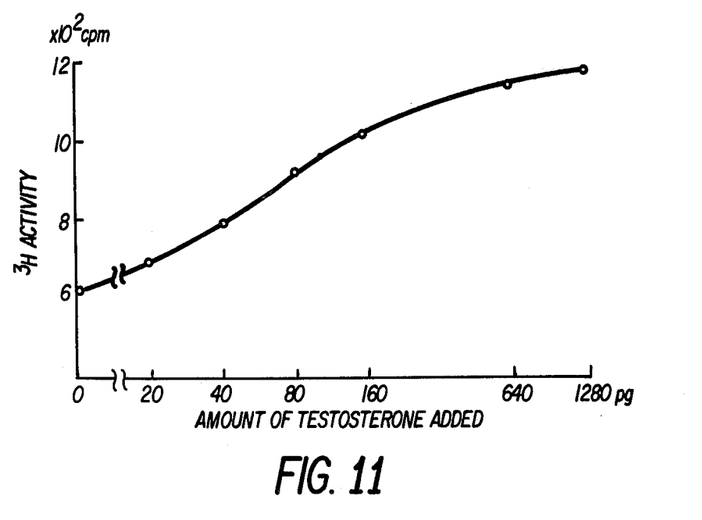

According to the general method as described in Example 4, the RIA was carried out under the following conditions. From the resulting data, there was drawn the calibration curve of testosterone as shown in FIG. 11.

Insolubilized antibody

[S. cerevisiae cell walls]-[anti-testosterone-3-oxime-BSA rabbit antibody] which was prepared in Example 2.

Labeled antigen

[$^3$H]-[testosterone] . . . 8.8 pg (1,700 cpm)

Unlabeled antigen

Standard testosterone . . . 0–1.3 ng
The time of the antigen-antibody reaction . . . 3 hours.

EXAMPLE 15

Measurement of haloperidol

Figure 12:
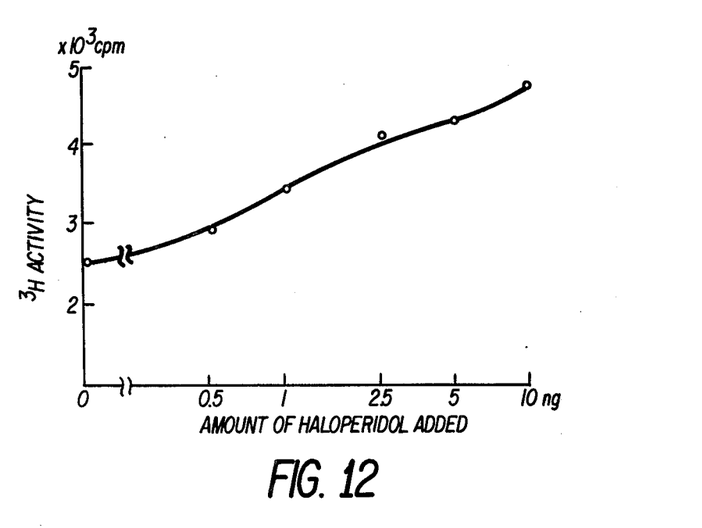

According to the general method as described in Example 4, the RIA was carried out under the following conditions. From the resulting data, there was drawn the calibration curve of haloperidol as shown in FIG. 12.

Insolubilized antibody

[S. cerevisiae cell walls]-[anti-3-(p-fluorobenzoyl)propionyl-BSA guinea pig antibody] which was prepared in Example 2.

Labeled antigen

[$^3$H]-[haloperidol] . . . 356 pg (7,300 cpm)

Unlabeled antigen

Standard haloperidol . . . 0–10 ng
The time of the antigen-antibody reaction . . . 30 minutes

Example 16

Measurement of human IgG

Figure 13:
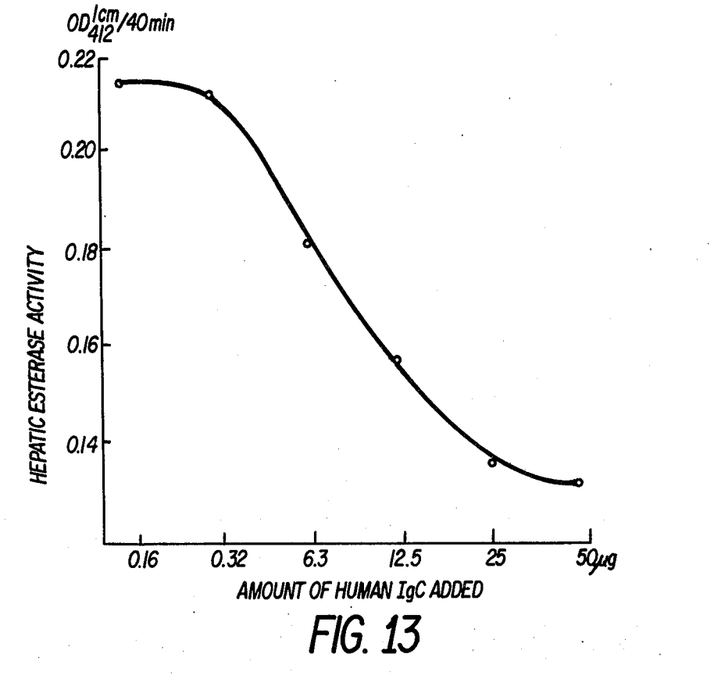

According to the general method as described in Example 4, the EIA was carried out under the following conditions. From the resulting data, there was drawn the calibration curve of human IgG as shown in FIG. 13, from which the amount of IgG in the human serum was calculated. The results are shown in the following Table 2.

Insolubilized antibody

[L. plantarum cell walls]-[anti-human IgG rabbit antibody] which was prepared in Example 1.

Labeled antigen

[Human IgG]-[hog hepatic esterase] which was prepared in Reference Example 3, (A) . . . $OD_{412}^{1\ cm}$/40 minutes=0.4

Unlabeled antigen

Standard human IgG . . . 0–50 μg
Human serum diluted 400 folds with 0.9% NaCl aqueous solution . . . 20 μl
The time of the antigen-antibody reaction . . . 30 minutes Table 2

| Human serum | Electrophoretic analysis (mg/ml) | EIA (mg/ml) |
| --- | --- | --- |
| A | 12.8 | 12.5 |
| B | 22.4 | 27.5 |
| C | 23.6 | 22.8 |
| D | 12.0 | 11.7 |

EXAMPLE 17

Measurement of serum T$_4$

Figure 14:
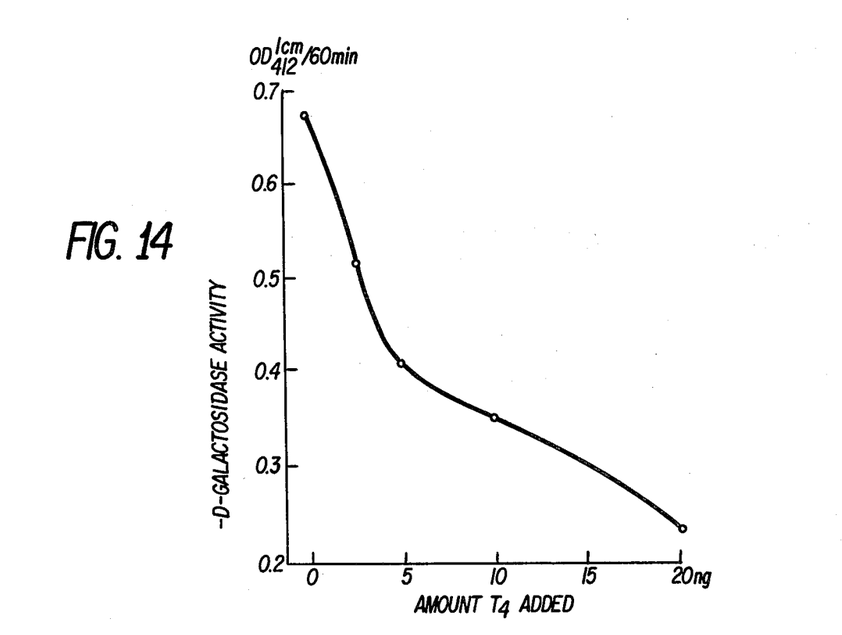

To a standard T$_4$ serum (50 μl) containing T$_4$ (0–20 ng) was added a mixture (0.2 ml) of a 20% trichloroacetic acid and a 0.5 N NaOH (1:3). The mixture was kept at room temperature for 10 minutes and then neutralized with a 1 M phosphate buffer (pH 7.0, 0.1 ml). To this solution were added a 0.4 M phosphate buffer (pH 7.0, 0.2 ml) containing 0.1% BSA, [T$_4$]-[β-D-galactosidase] (enzyme labeled antigen) (0.1 ml) prepared in Reference Example 3, (B-1), and [L. plantarum cell walls]-[anti-bovine thyroglobulin guinea pig antibody] (0.1 ml) prepared in Example 1. After incubating the mixture at 37° C. for 90 minutes, the reaction mixture was centrifuged (1,500×g, 10 minutes), and the precipitate was washed well with 0.9% NaCl (2 mil). To the precipitate were added a 0.1 M phosphate buffer (pH 7.0, 0.8 ml) containing 1 mM MgCl$_2$ and a 0.7% 2-mercaptoethanol—0.4% o-nitrophenyl-β-D-galactopyranoside (0.2 ml). The mixture was incubated at 45° C. for 60 minutes, and then the reaction was stopped by addition of a 0.2 M K$_2$HPO$_4$—NaOH buffer (pH 11.0, 2.5 ml). After the reaction mixture was centrifuged (1,500×g, 10 minutes), the optical density (O.D.) of the supernatant was measured at 410 nm. A standard calibration curve for serum T$_4$ assay by EIA thus obtained is shown in Fig. 14.

EXAMPLE 18

Measurement of human serum T$_4$

T$_4$ levels of human serum samples measured by EIA as described in Example 17 were compared with these obtained by the use of T$_4$ RIA KIT (Abbott Laboratories; U.S.A.). The results are shown in Table 3.

Table 3

| human serum samples | T4 RIA KIT (μg/dl) | EIA (μg/dl) |
|---|---|---|
| A | 2.6 | 3.2 |
| B | 6.8 | 8.4 |
| C | 9.7 | 10.3 |
| D | 12.3 | 16.0 |
| E | 19.0 | 23.0 |

EXAMPLE 19

Reagents and assay method for serum phenobarbital

Reagents

[A] Buffer solution: 0.2 M Tris-HCl—0.9% NaCl (pH 7.0)

[B] Standard phenobarbital solution: a solution of phenobarbital (1 μg) in [A] (1 ml)

[C] Enzyme labeled antigen: a 0.02 M Tris-HCl—0.9% NaCl—0.2% BSA—0.1% NaN$_3$ solution (pH 7.0) which contains [phenobarbital]-[β-D-galactosidase] prepared in Reference Example 3, (C) (25 μg/ml as β-D-galactosidase)

[D] Anti-phenobarbital insolubilized antibody: a 0.02 M Tris-HCl—0.9% NaCl—0.2% BSA—0.1% NaN$_3$ solution (pH 7.0) which contains antiphenobarbital insolubilized antibody prepared in Example 3 (10 mg/ml as the cell walls)

[E] Substrate solution: a 0.16% o-nitrophenyl-β-D-galactopyranoside—0.2 mM MgCl$_2$—0.3% β-mercaptoethanol—0.06 M potassium phosphate solution (pH 7.0).

[F] Enzyme reaction-stopping reagent: a 0.1 M potassium phosphate buffer (pH 10.3)

Assay Method

Into glass centrifuge tubes (2×10 cm) $X_1 \ldots X_n$ for standard phenobarbital calibration curve and $Y_1 \ldots Y_m$ for samples was added the buffer solution [A] (1 ml).

A prescribed amount (0–500 ng) of the standard phenobarbital solution [B] which was diluted with the buffer solution [A] by a two fold dilution method was added to the tubes $X_1$–$X_n$, and an appropriate amount of sample (for instance, in case of human serum, 50 μl after 50 fold dilution of the sample with the buffer solution [A]) was added to the tubes $Y_1 \ldots Y_m$. To all the tubes, were added the enzyme labeled antigen [C] (50 μl) and the anti-phenobarbital insolubilized antibody [D] (50 μl). In case the sample was a human serum of patient, there was added a normal human serum (100 μl) containing no phenobarbital which was diluted 10 folds. After mixing them well, the mixture was incubated at 5° C. for 30 minutes, centrifuged (1,500×g, 10 minutes), and the supernatant was removed. The precipitate was washed two times with the buffer solution [A] (1 ml) by centrifugation.

To the resulting precipitate was added the substrate solution [E] (0.5 ml) and the mixture was incubated at 37° C. for 15 or 30 minutes, and thereto was added the enzyme reaction-stopping reagent [F] (2 ml) and centrifuged. Absorption of the supernatant was measured at 412 nm. From the resulting data, there was drawn a standard calibration curve and then the level of phenobarbital in sample was calculated.

EXAMPLE 20

Effect of other anti-epileptic drugs on EIA for phenobarbital

Figure 15:
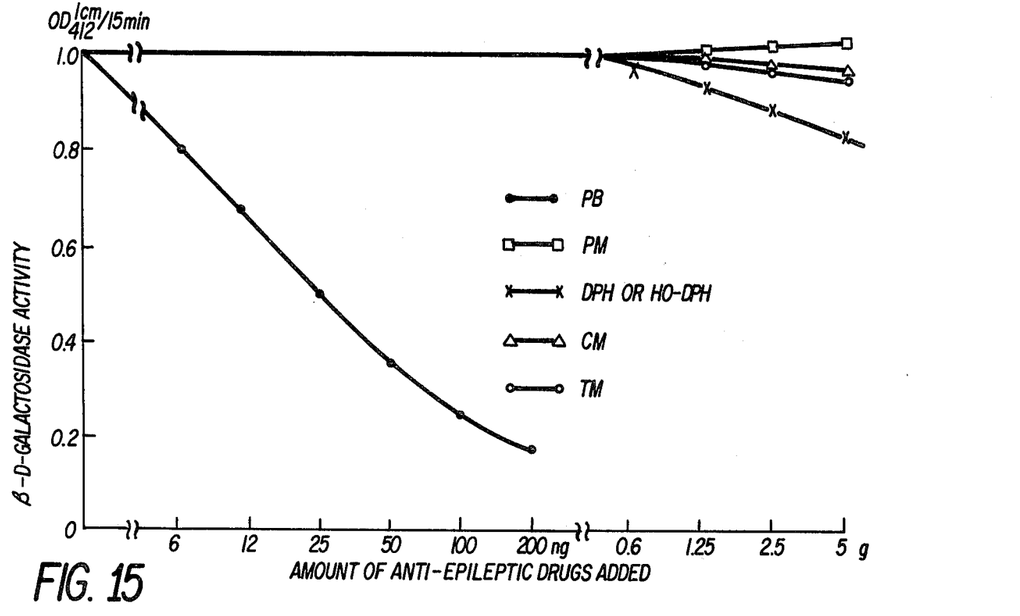

In the presence of various amount of phenobarbital (PB), DPH, p-hydroxy-diphenylhydantoin (HO-DPH), trimetadione (TM), carbamazepin (CM) and primidon (PM), the antigen-antibody reaction was carried out in the same manner as described in Example 19. The enzyme activity of the enzyme labeled antigen bound to the insolubilized antibody was measured. The results are shown in FIG. 15. As is shown in FIG. 15, the standard curve for phenobarbital assay was not affected by 0.4–10 μg of the above anti-epileptics including their metabolites.

EXAMPLE 21

Precision of the EIA

Phenobarbital levels in 3 human serum samples were measured 10 times by the EIA under the conditions as described in Example 19, and the constant of variation (CV) was calculated. The results are shown in Table 4. Besides, phenobarbital levels in other 3 human serum samples were measured once a day for 5 successive days by the EIA in the same manner as described in Example 19, and the variation of within a day or between days was measured. The results are shown in Table 5. As is shown in Table 5, the constant of variation (CV) in the EIA was within 10%.

Table 4

| Sample | G.C. (μg/ml) | EIA X ± SD* (μg/ml) | CV (%) |
|---|---|---|---|
| a | 10.4 | 9.2 ± 0.4 | 4.3 |
| b | 22.4 | 21.0 ± 0.9 | 4.2 |
| c | 32.0 | 36.8 ± 2.0 | 5.4 |

*X is "mean", SD is "standard deviation".

Table 5

| Sample | G.C. (μg/ml) | EIA 1 | 2 | 3 (μg/ml) | 4 | 5 days | X ± SD (μg/ml) | CV (%) |
|---|---|---|---|---|---|---|---|---|
| d | 5.5 | 5.1 | 5.5 | 5.3 | 5.6 | 5.0 | 5.3 ± 0.2 | 3.7 |
| e | 15.1 | 15.4 | 16.3 | 15.0 | 16.0 | 18.5 | 16.2 ± 1.2 | 7.0 |
| f | 27.2 | 27.0 | 26.0 | 28.5 | 29.0 | 25.1 | 27.0 ± 1.5 | 5.0 |

EXAMPLE 22

Measurement of phenobarbital in human serum

Figure 16:
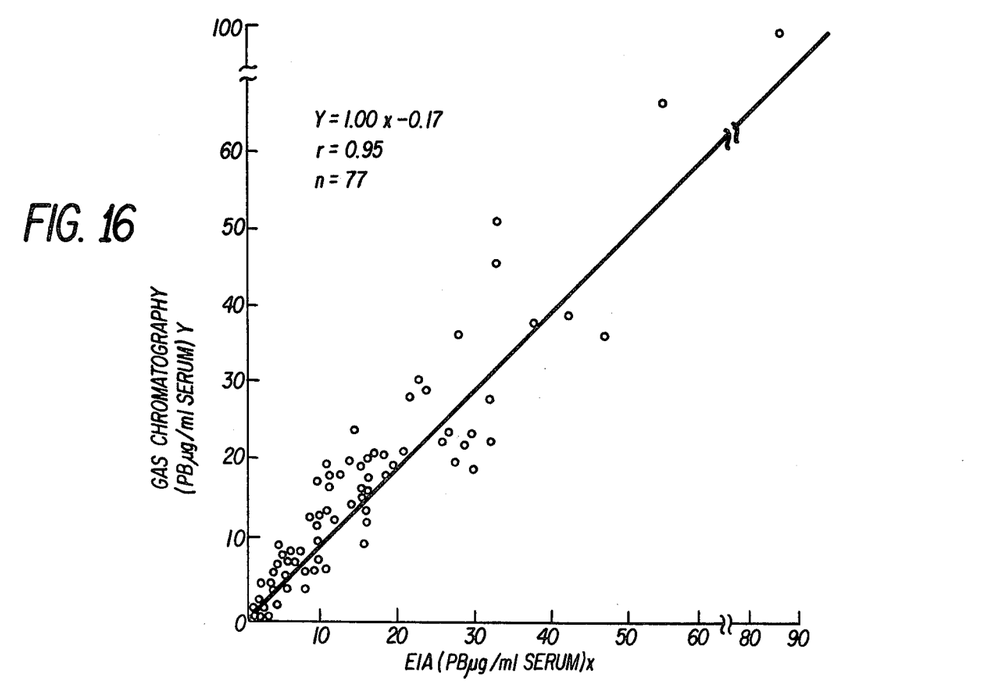

Phenobarbital in 77 human sera from patients who took orally three anti-epileptic drugs, phenobarbital (PB) DPH and primidon (PM) was measured by both EIA and gas chromatography. The phenobarbital levels obtained by the two methods were correlated well as shown in FIG. 16.

EXAMPLE 23

Preparation of an EIA kit suitable for the measurement of phenobarbital (A) Buffer solution:

To 100 glass bottles (30 ml volume) with a cap was added a 0.2 M Tris-HCl—9% NaCl buffer (pH 7.0, each 25 ml). When used, the content of the bottle is dissolved in water so as to make a final volume of 250 ml, which is used as the buffer solution [A] as in Example 19.

(B) Standard phenobarbital ethanol solution:

To 100 glass bottles (6 ml volume) with a cap was added a solution of phenobarbital (500 μg) in ethanol (5 ml). When used, it is diluted with the buffer solution [A] by a two fold dilution method.

(C) Enzyme labeled antigen:

To 100 glass bottles (6 ml volume) with a cap was added the enzyme labeled antigen [C] as described in Example 19 (each 5.2 ml).

(D) Anti-phenobarbital insolubilized antibody:

To 100 glass bottles (6 ml volume) with a cap was added the anti-phenobarbital insolubilized antobody [D] as described in Example 19 (each 5.2 ml).

(E) Substrate solution:

To 100 glass bottles with 2 ml volume was added o-nitrophenyl-β-D-galactopyranoside powder (each 88 mg). The bottles were sealed. When used, the content of the bottles is dissolved in a 0.2 mM $MgCl_2$—0.3% β-mercaptoethanol—0.06 M potassium phosphate buffer (pH 7.0, 52 ml) to give the substrate solution [E] as described in Example 19.

(F) Enzyme reaction-stopping reagent:

To 100 glass bottles (25 ml volume) with a cap was added a 1 M potassium phosphate buffer (pH 10.3, each 22 ml). When used, it is diluted with water so as to make a final volume of 220 ml, which is used as the enzyme reaction-stopping reagent [F] as described in Example 19.

There are prepared 100 sets of the kit consisting of each one bottle of the above (A) to (F), each of which is used for 100 phenobarbital assays in the same manner as described in Example 19.

EXAMPLE 24

Preparation of an EIA kit suitable for the measurement of DPH (1) Insolubilized antibody:

In the same manner as described in Example 1, there was prepared a [*L. plantarum* cell walls]-[anti-diphenylacetyl-BSA rabbit antibody]—0.1% BSA—0.9% NaCl—0.02 M Tris-HCl buffer (pH 7.0, 11 ml). The insolubilized antibody solution (each 2.5 ml) was added to 4 brown bottles with 10 ml volume and freeze-dried, whose air was replaced with nitrogen gas, and was reserved in the sealed state. When this product was kept at 50° C. for 2 months, no decrease in the power of antibody was observed. When one bottle is diluted with water (5.0 ml), 50 μl of the solution corresponds to the insolubilized antibody containing about 500 μg of cell walls.

(2) Enzyme labeled antigen:

In the same manner as described in Reference Example 3, (B-2), there was prepared a 0.2% BSA—0.1% $NaN_3$—0.05 M phosphate buffer (9 ml) containing [3,3-diphenylpropylamine]-[β-D-galactosidase] having $OD_{448}{}^{1cm}/20$ minutes = 810. The solution (each 2.0 ml) was added to 4 brown bottles with 10 ml volume. 20 μl of this solution corresponds to the enzyme labeled antigen of $OD_{448}{}^{1cm}/20$ minutes = 1.8.

An EIA kit suitable for the measurement of DPH consists of each one bottle of the above (1) and (2), which is used for about 100 DPH assays in the same manner as described in Example 5.

What is claimed is:

1. An insolubilized antibody for an enzyme immuno assay or radio immuno assay, which has characteristic infrared absorptions at around 1040 cm$^{-1}$, 1540 cm$^{-1}$ and 1640 cm$^{-1}$ comprising said antibody chemically bonded to cell wall debris of bacteria or yeasts whose shape is globular or rod-like.

2. The insolubilized antibody according to claim 1, wherein the antibody is chemically bonded to the cell wall debris of bacteria whose shape is globular or rod-like.

3. The insolubilized antibody according to claim 1, wherein the antibody is chemically bonded to the cell wall debris of yeasts whose shape is globular or rod-like.

4. The insolubilized antibody according to claim 2, wherein the globular or rod-like bacteria belong to the order Eubacteriales.

5. The insolubilized antibody according to claim 2, wherein the globular or rod-like bacteria are a member selected from the group consisting of the genus Streptococcus, Staphylococcus, Micrococcus, Lactobacillus, Bacillus, Escherichia and Achromobacter.

6. The insolubilized antibody according to claim 2, wherein the globular or rod-like bacteria are a member selected from the group consisting of the species of *Streptococcus faecalis, Streptococcus salivarius, Streptococcus mutans, Staphylococcus aureus, Micrococcus lysodeiticus, Micrococcus roseus, Lactobacillus plantarum, Bacillus subtilis, Bacillus megatherium, Escherichia coli* and *Achromobacter aquamarinus.*

7. The insolubilized antibody according to claim 2, wherein the bacteria belong to the species *Lactobacillus plantarum.*

8. The insolubilized antibody according to claim 3, wherein the globular or rod-like yeasts are a member selected from the group consisting of the genus Saccharomyces, Pichia and Schizosaccharomyces.

9. The insolubilized antibody according to claim 3, wherein the globular or rod-like yeasts are a member selected from the group consisting of the species of *Saccharomyces cerevisiae, Pichia polymorpha* and *Schizosaccharomyces pombe.*

10. The insolubilized antibody according to claim 3, wherein the yeasts belong to the species *Saccharomyces cerevisiae.*

11. The insolubilized antibody according to claim 1, wherein the antibody is a member selected from the group consisting of the antibodies against the following antigens: hormones, enzymes, virus-specific antigen, tumor antigen, immunogrobulins, human- or bovine-serum albumin and haptens.

12. The insolubilized antibody according to claim 11, wherein the hormons are a member selected from the group consisting of insulin, tri- or tetra-iodothyronine and human chorionic gonadotropin.

13. The insolubilized antibody according to claim 11, wherein the haptens are a member selected from the group consisting of diphenylhydantoin, phenobarbital, testosterone and haloperidol.

14. The insolubilized antibody of claim 1 wherein the antibody is chemically bonded to cell wall debris with a binding agent or by oxidizing the cell wall debris with an oxidizing agent and then reacting the resulting oxidation product with the antibody.

15. The insolubilized antibody of claim 14 wherein the antibody is chemically bonded to the cell wall debris of bacteria.

16. The insolubilized antibody of claim 14 wherein the antibody is chemically bonded to the cell wall debris of yeast.

17. The insolubilized antibody according to claim 14, wherein the binding agent is glutaraldehyde.

18. The insolubilized antibody according to claim 14, wherein the oxidizing agent is sodium periodate.

19. The insolubilized antibody according to claim 11, wherein the antibody is a antibody against a hapten which has a partial structure common to that of an antigen to be measured.

20. A kit for an enzyme immuno assay or radio immuno assay, which comprises the following two components:
   Component A: an insolubilized antibody which has characteristic infrared absorptions at around 1040 $cm^{-1}$, 1540 $cm^{-1}$ and 1640 $cm^{-1}$ and comprises an antibody chemically bonded to cell wall debris of bacteria or yeasts whose shape is globular or rod-like, and
   Component B: an enzyme labeled antigen or a radio isotope labeled antigen.

21. The kit according to claim 20, which is suitable for the assay of any one of the following substances: insulin, human chorionic gonadotropin, immunogrobulins, human serum albumin, tri- or tetra-iodothyronine, diphenylhydantoin, phenobarbital, testosterone and haloperidol.

22. The kit according to claim 21, which comprises the following components:
   Component A: an insolubilized antibody comprising an antibody against diphenylhydantoin or a compound having a partial structure common to that of diphenylhydantoin, said antibody being chemically bonded with cell wall debris of Lactobacillus plantarum and
   Component B: an enzyme labeled antigen comprising $\beta$-D-galactosidase bonded to diphenylhydantoin or a compound having partial structure common to that of diphenylhydantoin.

23. The kit according to claim 21, which comprises the following components:
   Component A: an insolubilized antibody comprising an antibody against phenobarbital or a compound having partial structure common to that of phenobarbital, said antibody being chemically bonded to cell wall debris of Saccharomyces cerevisiae, and
   Component B: an enzyme labeled antigen comprising $\beta$-D-galactosidase bonded to diazonium salt of m-amino-phenobarbital.

24. In a method for conducting an enzyme immuno assay or radio immuno assay, which comprises subjecting an enzyme-or radio isotope-labeled antigen, an unlabeled antigen and an antibody to a competitive antigen-antibody reaction in a buffered solution, separating the enzyme- or ratio isotope-labeled antigen bound to the antibody from the free labeled antigen, and determining the amount of the unlabeled antigen by measuring an enzyme activity or radio activity of either the labeled antigen bound to the antibody or the free labeled antigen, the improvement wherein the antibody is an insolubilized antibody which has characteristic infrared absorptions at around 1040 $cm^{-1}$, 1540 $cm^{-1}$, and 1640 $cm^{-1}$ and comprises an antibody chemically bonded to cell wall debris of bacteria or yeasts whose shape is globular or rod-like.

* * * * *